(12) United States Patent
Repka (10) Patent No.: US 11,603,878 B2
(45) Date of Patent: Mar. 14, 2023

(54) MOUNT INTERFACE FOR A MEDICAL DEVICE

(71) Applicant: Maquet Cardiopulmonary GmbH, Rastatt (DE)

(72) Inventor: William James Repka, Parsippany, NJ (US)

(73) Assignee: MAQUET CARDIOPULMONARY GmbH, Rastatt (DE)

( * ) Notice: Subject to any disclaimer, the term of this patent is extended or adjusted under 35 U.S.C. 154(b) by 0 days.

(21) Appl. No.: 17/225,776

(22) Filed: Apr. 8, 2021

(65) Prior Publication Data
US 2021/0222718 A1     Jul. 22, 2021

Related U.S. Application Data

(62) Division of application No. 15/570,999, filed as application No. PCT/EP2016/060783 on May 12, 2016, now Pat. No. 11,028,869.

(Continued)

(51) Int. Cl.
*F16B 21/09*     (2006.01)
*A61M 1/14*      (2006.01)
*A61M 1/36*      (2006.01)

(52) U.S. Cl.
CPC .......... *F16B 21/09* (2013.01); *A61M 1/14* (2013.01); *A61M 1/367* (2013.01);
(Continued)

(58) Field of Classification Search
USPC ..... 70/387, 403, 453, 454; 292/340, 341.15, 292/163, 156, 1, DIG. 37, DIG. 21;
(Continued)

(56) References Cited

U.S. PATENT DOCUMENTS

| | | | | |
|---|---|---|---|---|
| 3,529,860 A | * | 9/1970 | Lionel | ..................... F16B 21/09 160/402 |
| 4,504,167 A | | 3/1985 | Nakanishi | |
| 6,234,708 B1 | * | 5/2001 | Beck | ......................... F16B 7/22 482/16 |
| 2006/0251473 A1 | * | 11/2006 | Tyski | .................... F16B 5/0642 403/408.1 |

(Continued)

FOREIGN PATENT DOCUMENTS

| GB | 2513369 A | 10/2014 |
|---|---|---|
| JP | 38-024326 Y | 11/1963 |

(Continued)

OTHER PUBLICATIONS

Official Action issued in Japanese Application No. 2017-558686 dated Mar. 30, 2020, 8 pages.

(Continued)

*Primary Examiner* — Alfred J Wujciak (57) ABSTRACT

A mount interface is described that includes a latch; and a latching assembly configured to receive the latch so as to lock the latch at a set position with respect to the latching assembly, wherein the latching assembly includes a housing provided with an irregular orifice configured to receive the latch; a first plug disposed in the housing so that a first portion of the irregular orifice overlies the first plug; and a second plug disposed in the housing adjacent the first plug so that a second portion of the irregular orifice overlies the second plug. Such a mount interface provides rapid and secure locking of a latch to the latching assembly.

4 Claims, 8 Drawing Sheets

Related U.S. Application Data (60) Provisional application No. 62/160,728, filed on May 13, 2015.

(52) U.S. Cl.
CPC ........ *A61M 1/3666* (2013.01); *A61M 1/3667* (2014.02); *A61M 2205/505* (2013.01); *A61M 2209/08* (2013.01); *A61M 2209/082* (2013.01); *A61M 2209/086* (2013.01)

(58) Field of Classification Search
USPC .............. 403/322.1, 322.4, 327; 248/221.11, 248/221.12, 222.11, 222.12, 222.13, 248/222.51, 222.41
See application file for complete search history.

(56) References Cited

U.S. PATENT DOCUMENTS

| | | | | |
|---|---|---|---|---|
| 2008/0107479 A1* | 5/2008 | Yang | ................. | H05K 7/20172 403/155 |
| 2014/0127063 A1 | 5/2014 | Petersen et al. | | |
| 2014/0255093 A1* | 9/2014 | Yang | ......................... | F16B 5/07 403/382 |
| 2016/0108945 A1* | 4/2016 | Yang | ....................... | F16B 21/09 403/359.6 |

FOREIGN PATENT DOCUMENTS

| | | | |
|---|---|---|---|
| JP | 59-153708 | U | 10/1984 |
| JP | 2015073589 | A | 4/2015 |
| WO | 2004064896 | A2 | 8/2004 |
| WO | 2004/064896 | A3 | 10/2004 |
| WO | 2012162515 | A2 | 11/2012 |
| WO | 2016180950 | A2 | 11/2016 |

OTHER PUBLICATIONS

Notification to Grant Patent Right for Invention issued in Chinese Application No. 201680027819.4 dated Jun. 16, 2020, 4 pages.
Search Report issued in Chinese Application No. 201680027819.4 dated Jun. 8, 2020, 3 pages.
Chinese Office Action (with English translation) and Chinese Search Report dated Nov. 6, 2019 during the prosecution of corresponding Chinese Patent Application No. 201680027819.4, 15 pages.
International Search Report and Written Opinion of corresponding International Application No. PCT/EP2016/060783 dated Jun. 20, 2017.
International Preliminary Report on Patentability of corresponding International Application No. PCT/EP2016/060783 dated Nov. 23, 2017.

* cited by examiner

MOUNT INTERFACE FOR A MEDICAL DEVICE

This application is divisional application of U.S. patent application Ser. No. 15/570,999, filed on Oct. 31, 2017 (now U.S. Pat. No. 11,028,869 B2), which is a national stage entry (under 35 USC 371) of PCT/EP/2016060783, filed May 12, 2016, which claims the benefit of priority to U.S. Provisional Patent Application 62/160,728, filed May 13, 2015. The disclosures of the above-identified patent applications and US patent are incorporated herein by reference in their entirety for all they disclose.

FIELD OF THE DISCLOSURE

The present disclosure pertains broadly to the field of mount interfaces, such as are used to mount one device to another device. More specifically, the field of this disclosure may be construed as directed to a mount interface for a medical device, such as may be mounted to the frame of a heart-lung machine.

BACKGROUND OF THE DISCLOSURE

There is an ever evolving need for mount interfaces that can be used to mount one kind of device to another kind of device. For example, in the field of heart-lung machines, various devices, such as a cardiac pump, are mounted to a frame of a heart-lung machine via a connector, such as a compression ring clamping assembly. However, connectors constructed using a compression ring clamping assembly are difficult to use depending upon the orientation of the connector relative to the frame and the ground. Consequently, in the case of cardiac pump failure, there is a need to be able to release the connector easily and quickly so that the failed cardiac pump can be efficiently replaced with a new and operable cardiac pump, and the new cardiac pump quickly and easily secured to the frame by the connector, in as short a time as possible and regardless of the orientation of the cardiac pump with respect to the frame of the heart-lung machine.

Moreover, the parts used to assemble connectors employing a compression ring clamping assembly are not inexpensive to manufacture, and are not inexpensive to assemble. Therefore, there is a need for a mount interface for a device, such as may mount a cardiac pump to the frame of a heart-lung machine, that is inexpensive to manufacture, and simple to assemble so as to minimize the costs associated with its assembly. This disclosure is directed to describing embodiments directed to apparatuses and methods that overcome the deficiencies of compression ring clamping assemblies.

SUMMARY OF THE DISCLOSURE

In accordance with a non-limiting embodiment of this disclosure, a mount interface is provided that includes: a latch; and a latching assembly configured to receive the latch so as to lock the latch at a predetermined position with respect to the latching assembly, wherein the latching assembly includes a housing provided with an irregular orifice configured to receive the latch; a first plug disposed in the housing so that a first portion of the irregular orifice overlies the first plug; and a second plug disposed in the housing adjacent the first plug so that a second portion of the irregular orifice overlies the second plug. In accordance with a second non-limiting embodiment of this disclosure, the above first non-limiting embodiment is modified so that when the latch is locked at the set position, the latch is in contact with the first plug and the second plug.

In accordance with a third non-limiting embodiment of this disclosure, the first and second non-limiting embodiments are modified so that the first plug and the second plug are moveable in a transverse direction parallel to one another. In accordance with a fourth non-limiting embodiment of this disclosure, the first, second and third non-limiting embodiments are further modified so that the first plug and the second plug are each spring-biased towards an external surface of the housing. In accordance with a fifth non-limiting embodiment of this disclosure, the first, second, third and fourth non-limiting embodiments are further modified so that when the latch is disengaged from the latching assembly the first plug and the second plug are each spring-biased into a position in which at least one surface of the first plug and at least one surface of the second plug are substantially flush with the external surface of the housing. In accordance with a sixth non-limiting embodiment of this disclosure, the first, second, third, fourth and fifth non-limiting embodiments are further modified so that when the at least one surface of the first plug and the at least one surface of the second plug are substantially flush with the external surface of the housing, then the first plug abuts the second plug. In accordance with a seventh non-limiting embodiment of this disclosure, the first, second, third, fourth, fifth and sixth non-limiting embodiments are further modified so that when the latch is locked in the set position, then the first plug and the second plug do not abut one another.

In accordance with an eighth non-limiting embodiment of this disclosure, the first, second, third, fourth, fifth, sixth and seventh non-limiting embodiments are modified so that the irregular orifice is keyhole shaped with a circular portion contiguous with an elongated portion. In accordance with a ninth non-limiting embodiment of this disclosure, the first, second, third, fourth, fifth, sixth, seventh and eighth non-limiting embodiments are further modified so that the circular portion overlies both the first plug and the second plug and the elongated portion overlies the second plug and not the first plug.

In accordance with a tenth non-limiting embodiment of this disclosure, the first, second, third, fourth, fifth, sixth, seventh, eighth and ninth non-limiting embodiments are modified so as to further include a non-linear link connected at one end to the first plug and pivotally connected to the housing. In accordance with an eleventh non-limiting embodiment of this disclosure, the first, second, third, fourth, fifth, sixth, seventh, eighth, ninth and tenth non-limiting embodiments are further modified so that the non-linear link is connected at a second end to a release button so that when pressure is exerted on the release button, the release button is depressed towards an interior of the housing and the non-linear link pivots so as to move the first plug away from the first portion of the irregular orifice. In accordance with a twelfth non-limiting embodiment of this disclosure, the first, second, third, fourth, fifth, sixth, seventh, eighth, ninth, tenth and eleventh non-limiting embodiments are further modified so that the non-linear link comprises a linear portion connected to a minor bend portion by a major bend portion. In accordance with a thirteenth non-limiting embodiment of this disclosure, the first, second, third, fourth, fifth, sixth, seventh, eighth, ninth, tenth, eleventh and twelfth non-limiting embodiments are further modified so that the latch is cylindrical and includes a neck portion having a diameter that is smaller than a diameter of a head portion that is connected to the neck portion, and wherein the diameter of the head portion is smaller than a diameter of the circular portion of the irregular orifice and the diameter of the head portion is larger than a maximum width of the elongated portion of the irregular orifice.

In accordance with a fourteenth non-limiting embodiment of this disclosure, a heart-lung machine is provided, which includes: a frame, and a mount interface connected to the frame, wherein the mount interface is the mount interface according to any one of the first, second, third, fourth, fifth, sixth, seventh, eighth, ninth, tenth, eleventh, twelfth and thirteenth non-limiting embodiments of this disclosure. In accordance with a fifteenth non-limiting embodiment of this disclosure, the fourteenth non-limiting embodiment is modified so that the latch is connected to the frame and the latching assembly is connected to a medical device, or wherein the latch is connected to the medical device and the latching assembly is connected to the frame. In accordance with a sixteenth non-limiting embodiment of this disclosure, the fourteenth and fifteenth non-limiting embodiments are further modified so that the medical device is selected from the group consisting of a centrifugal blood pump, a venous reservoir, an oxygenator, a venous clamp and a medical graphical user interface display apparatus.

In accordance with a seventeenth non-limiting embodiment of this disclosure, a method of locking a latch to a latching assembly of a mount interface is provided, wherein the method comprises the steps of: (a) engaging a latch with a spring-biased first plug of the latching assembly; (b) pressing the latch against the spring-biased first plug so as to insert the latch into a first portion of an irregular orifice of a housing of the latching assembly while moving the spring-biased first plug from a spring-biased rest position to a second position and while moving a spring-biased second plug from a spring-biased rest position to a second position; and (c) sliding the latch from the first portion of the irregular orifice to a second portion of the irregular orifice so the latch presses against the spring-biased second plug and not against the spring-biased first plug. In accordance with an eighteenth non-limiting embodiment of this disclosure, the seventeenth non-limiting embodiment is further modified so that the first portion of the irregular orifice is circular and the second portion of the irregular orifice is non-circular, and when the latch is in the second portion of the irregular orifice, the spring-biased second plug pushes the latch against the housing. In accordance with a nineteenth non-limiting embodiment of this disclosure, the seventeenth and eighteenth non-limiting embodiments are modified so the method further includes the step of locking the latch in the second portion of the irregular orifice when the spring-biased first plug moves back to the spring-biased rest position from the second position. In accordance with a twentieth non-limiting embodiment of this disclosure, the seventeenth, eighteenth and nineteenth non-limiting embodiments are further modified so that the method further includes the steps of pressing a release button so as to cause the spring-biased first plug to move away from the spring-biased rest position and back to the second position in order to release the latch from the second portion of the irregular orifice; sliding the latch from the second portion of the irregular orifice to the first portion of the irregular orifice; and disengaging the latch from the spring-biased first plug of the latching assembly.

DETAILED DESCRIPTION OF EMBODIMENT(S)

Various embodiments in accordance with this disclosure are described with reference to the figures, in which like parts are designated by like reference numbers. The drawings described herein constitute non-limiting illustrations.

As shown in FIGS. 1 to 5, a mount interface 10 includes a latch 12 and a latching assembly 14, which may engage each other and subsequently disengage from one another. In accordance with an embodiment of this disclosure, the latch 12 is connected to the frame 16 of a first medical device, such as a heart-lung machine, and the latching assembly 14 is connected to the housing 18, or made integral to the housing, of a second medical device, such as a cardiac pump. In accordance with an embodiment of this disclosure, the latch is connected to the housing of the second medical device and the latching assembly is connected to the frame, or made integral to the frame, of the second medical device. The examples provided with respect to the first medical device and the second medical device are merely illustrative and are not limiting in any way. In fact, in accordance with this disclosure, the mount interface 10 may be used to mount two non-medical devices together, or to mount two medical devices together, or to mount a non-medical device and a medical device together.

Figure 4:
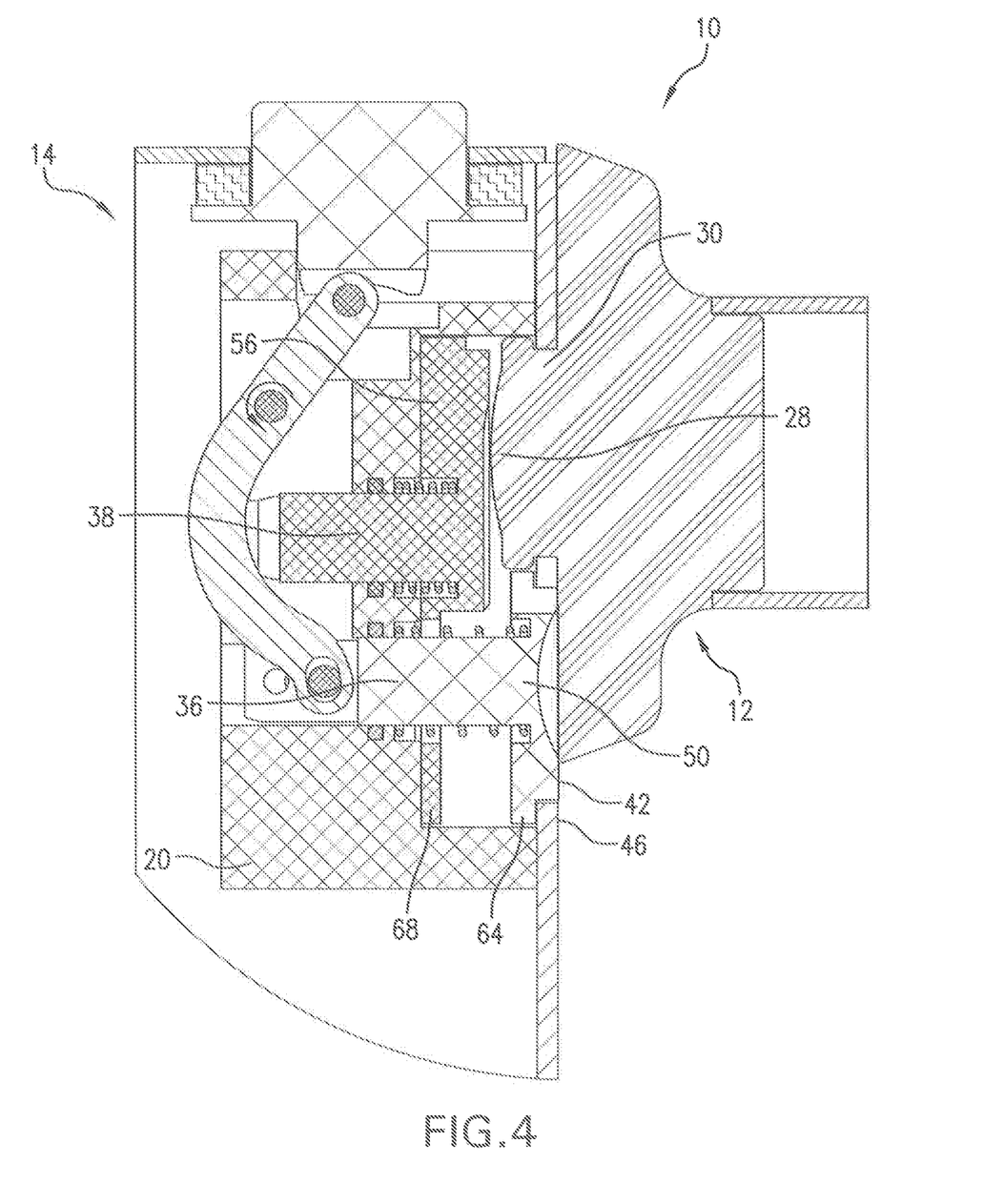
FIG. 4 is a cross-sectional view of the mount interface shown in FIG. 1, wherein the latch is in the third position and the first plug is in the spring-biased rest position.
Figure 6:
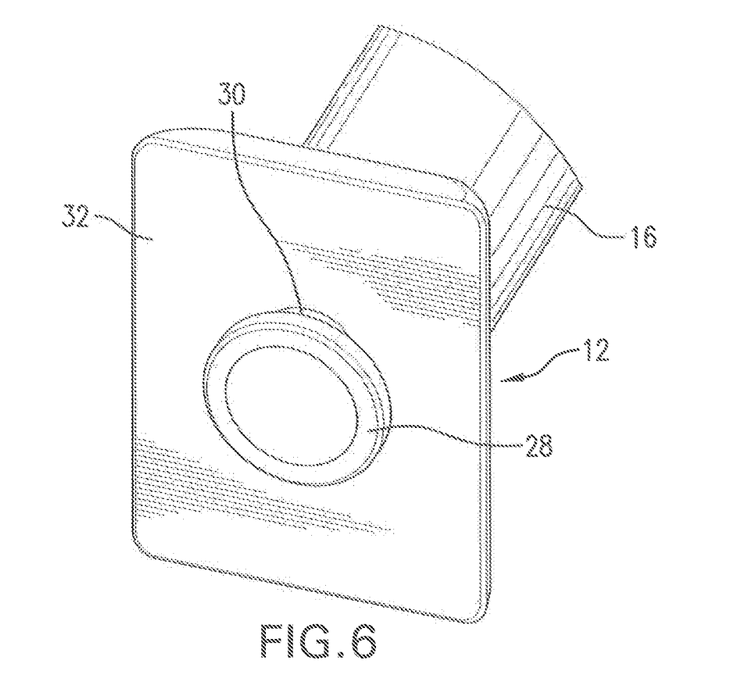
FIG. 6 is a perspective view of a latch embodiment of this disclosure.

The latching assembly 14 is configured to receive the latch 12 so as to lock the latch at a set position with respect to the latching assembly, as shown in FIG. 4. In order to achieve this locked connection, the latching assembly 14 is provided with a housing 20 that is either connected to, integral with, or part of the housing 18 of the second device, or of the frame of the first device. The housing 20 is provided with an irregular orifice 22 formed therein and configured to receive the latch 12. In an embodiment, the irregular orifice 22 has a keyhole shape, which means that it includes a first portion 24 that is contiguous with a second elongated portion 26. In an embodiment, the elongated portion has a length that is greater than its width, and the first portion 24 is circular. The first portion 24 is illustrated in the drawings as circular; however, it may have other shapes such as a triangular-shape, a square-shape, a rectangular-shape, or any suitable polygon-shape. The first circular portion 24 is dimensioned so that its diameter is larger than the diameter of the head portion 28 of the latch 12. The latch 12 includes a neck portion 30 that connects the head portion 28 to the base portion 32, such as shown in FIG. 6. The neck portion 30 has a smaller diameter than the head portion 28 of the latch 12 for reasons that will be described later in this disclosure. The diameter of the neck portion 30 is dimensioned so as to be smaller than the minimum width of the elongated portion 26 of the irregular orifice 22 so the neck portion 30 may slide within the elongated portion 26. The elongated portion 26 may be constructed to include a taper, or it may be constructed without a taper. On the other hand, the head portion 28 is dimensioned so that its diameter is substantially larger than the maximum width of the elongated portion 26 of the irregular orifice 22 so that the head portion 28 cannot slip through the elongated portion 26 when the head portion 28 is in cavity 34.

The latch assembly 14 further includes two moveable plugs disposed in the cavity 34 formed in the housing 20. The first plug 36 is disposed in the housing 20 so that the first portion 24 of the irregular orifice 22 overlies the first plug, and the second plug 38 is disposed in the housing 20 adjacent the first plug 36 so that the second portion 26 of the irregular orifice 22 overlies the second plug 38. As evident from the drawings, some of the first portion 24 of the irregular orifice 22 may also overlie a portion of the second plug 38. In accordance with an embodiment of this disclosure, some of the second portion 26 may overlie a portion of the first plug 36.

Figure 1:
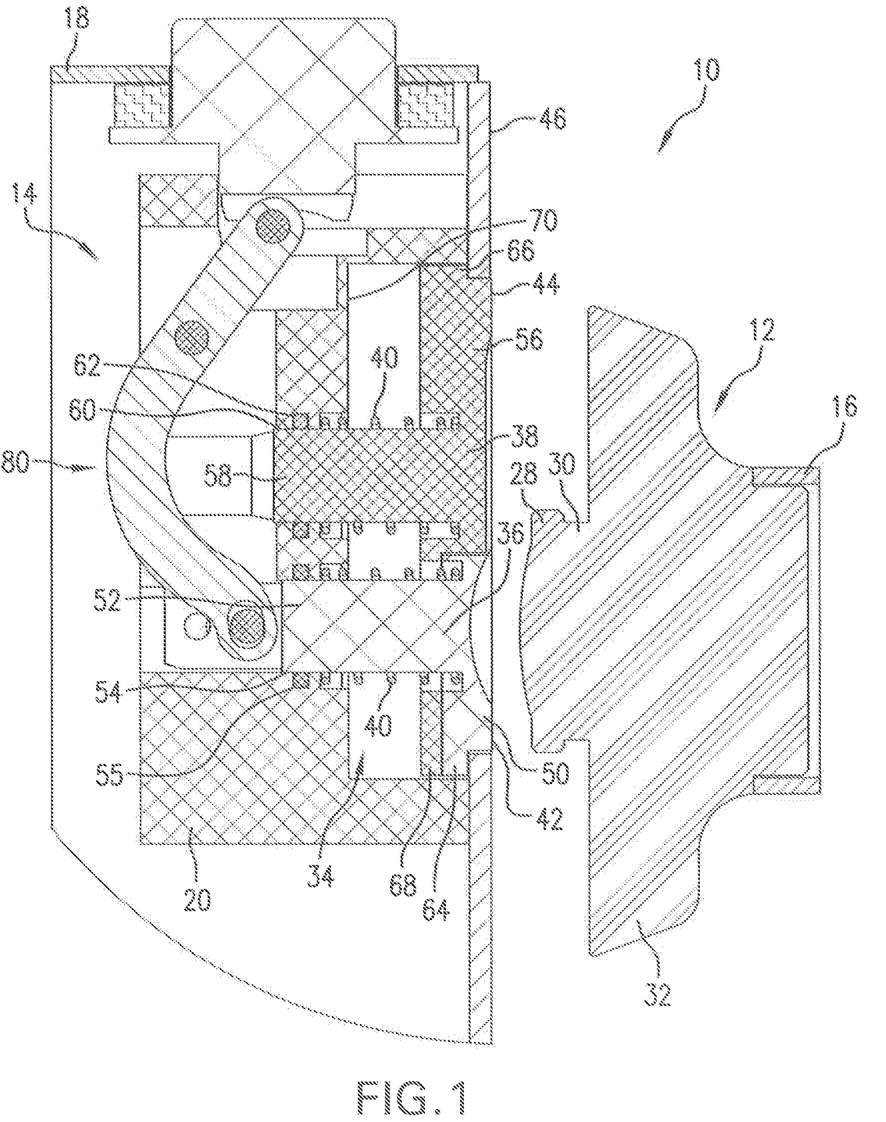
FIG. 1 is a cross-sectional view of a mount interface in accordance with an embodiment of this disclosure, wherein a latch is shown in a condition disengaged from a latching assembly.

Each of the first plug 36 and the second plug 38 is spring-biased by its own biasing spring 40 towards a spring-biased rest position, as shown in FIG. 1. It is to be appreciated that while the biasing spring 40 is shown in the illustrated embodiments as a coil spring, that any type of spring may be included. Furthermore, the term "spring" is intended to include any element, component, or device that is configured to exert a biasing force, and may be or include a coil spring, leaf spring, torsion spring, a portion of elastically deformable and resilient material such as a foam block, a pressurized chamber, magnets arranged to attract/repel the plugs, etc. When the first plug 36 is in the spring-biased rest position, at least a portion 42 of its external surface is substantially flush with the external surface 46 of the housing 20. When the second plug 38 is in the spring-biased rest position, at least a portion 44 of its external surface is substantially flush with the external surface 46 of the housing 20. When the first plug 36 and the second plug 38 are in the spring-biased rest position together, and substantially flush with the external surface 46 as shown in FIG. 1, the first plug 36 and the second plug 38 together plug, and substantially occlude, the irregular orifice 22 in order to prevent blood, other bodily fluids, and/or other substances, from entering cavity 34. The spring 40 biasing the first plug 36 towards the external surface 46 of the housing 20 may be disposed in a channel that is formed partly in the housing 20 and partly in the first plug 36. The spring 40 biasing the second plug 38 towards the external surface 46 of the housing 20 may be disposed in a channel that is formed partly in the housing 20 and partly in the second plug 38.

Figure 2:
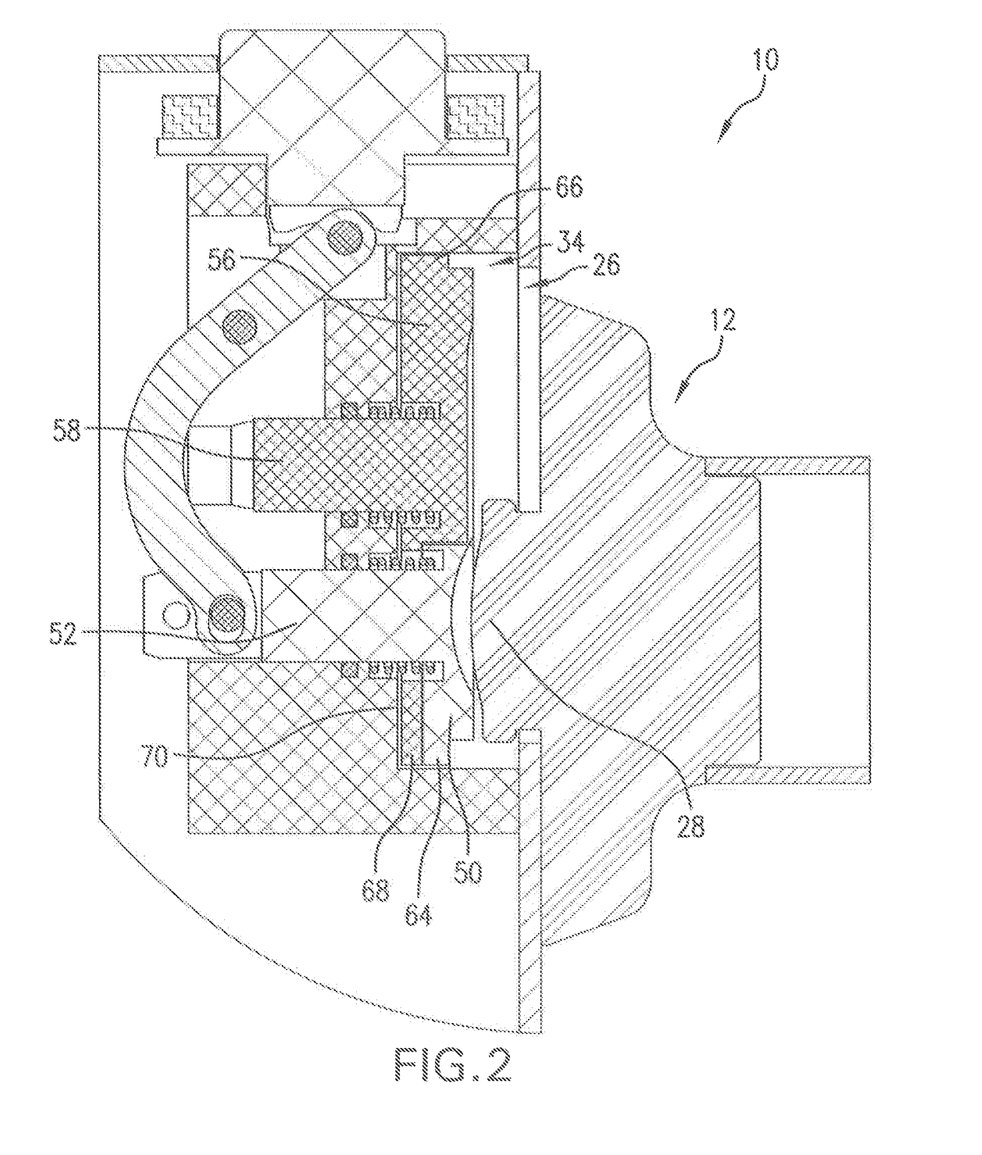
FIG. 2 is a cross-sectional view of the mount interface shown in FIG. 1, wherein the latch is shown in an engaged condition with the latching assembly.

As evident from FIGS. 1 and 2, each of the spring-biased plugs 36, 38 is moveable in a direction transverse to the plane of the irregular orifice 22 and parallel to one another. The first plug 36 has a head portion 50 connected to a tail portion 52, and is disposed to move in a channel 54 formed in the housing 20 that is provided with a seal SS, such as an O-ring. The second plug 38 has a head portion 56 connected to a tail portion 58, and is disposed to move in a channel 60 formed in the housing 20 that is provided with a seal 62, such as an O-ring. The seals 55 and 62 prevent blood, other fluids, and other substances, from penetrating beyond the cavity 34 of the latching assembly 14.

When the latch 12 is disengaged from the latching assembly 14, then the first plug 36 and the second plug 38 are each spring-biased into the position (i.e., the spring-biased rest position, which may also be referred to as a first position) in which at least one surface 42 of the first plug and at least one surface 44 of the second plug is substantially flush with the external surface 46 of the housing 20. When the at least one surface 42 of the first plug 36 and the at least one surface 44 of the second plug 38 are substantially flush with the external surface 46 of the housing, then the first plug 36 abuts the second plug 38. The head 50 of the first plug 36 is provided with a lip 64 that engages a portion of the housing 20 that forms the irregular orifice in order to limit the movement of the first plug 36 so that it stops at the spring-biased rest position. The head 56 of the second plug 38 is provided with a lip 66 that engages another portion of the housing 20 that forms the irregular orifice in order to limit the movement of the second plug 38 so that it stops at the spring-biased rest position.

When the latch 12 is aligned with the first portion 24 of the irregular orifice 22, the latch 12 may engage the head 50 of the first plug 36 so as to press against the head 50 and push the first plug 36 further into the cavity 34, as shown in FIG. 2, thereby compressing spring 40 and moving the tail portion 52 within the channel 54 formed in the housing 20. When this happens, the second plug 38 moves with the first plug 36 because the second plug 38 includes an extension 68 that extends from the head 56 and beneath the head 50 of the first plug 36. Consequently, when the latch 12 pushes the first plug 36 in the transverse direction further into the cavity 34, the head 50 of the first plug 36 engages the extension 38 of the second plug 38 and pushes the second plug 38 with it in the transverse direction. The first plug 36 and the second plug 38 may be moved by the latch 12 in the transverse direction to a tensioned-spring position, as shown in FIG. 2, which may be referred to as a second position, in which the head 50 of the first plug 36 and the head 56 of the second plug 38 have been pushed against the floor 70 of the cavity 34 by the latch 12. In this tensioned-spring position, each of the springs 40 has been forced into a configuration of greater tension, namely, a compressed configuration.

When the first plug 36 and the second plug 38 have been pushed into the tensioned-spring position by the latch 12, the head portion 28 of the latch 12, which is in the second position, is positioned within the cavity 34, and is in position to move laterally by sliding on the heads 50 and 56 of the first plug 36 and the second plug 38, respectively. When the latch 12 is slid on the heads 50, 56, the latch 12 moves from the first portion 24 of the irregular orifice 22 into the elongated portion 26 of the irregular orifice 22. In particular, latch 12 slides laterally with its neck portion 30 positioned in the irregular orifice 22, and its head portion 28 positioned within the cavity 34, and its base portion 32 disposed on the external surface 46 of the housing 20. Because of this positioning, the latch 12 is moveable laterally in the elongated portion 26 of the irregular orifice 22 without popping out of the irregular orifice 22. In fact, once the latch 12 has moved into the elongated portion 26 of the irregular orifice 22, the head portion 28 of the latch 12 is caught by the housing 20, more specifically by one or more walls of the housing, and cannot be removed directly from the elongated portion 26. In view of the geometry of the latch 12 and the irregular orifice 22, the head portion 28 of the latch 12 may only be removed from the cavity 34 when the latch 12 is disposed substantially within the first portion 24 of the irregular orifice 22, such as when the head portion 28 is in the second position (FIG. 2).

Figure 3:
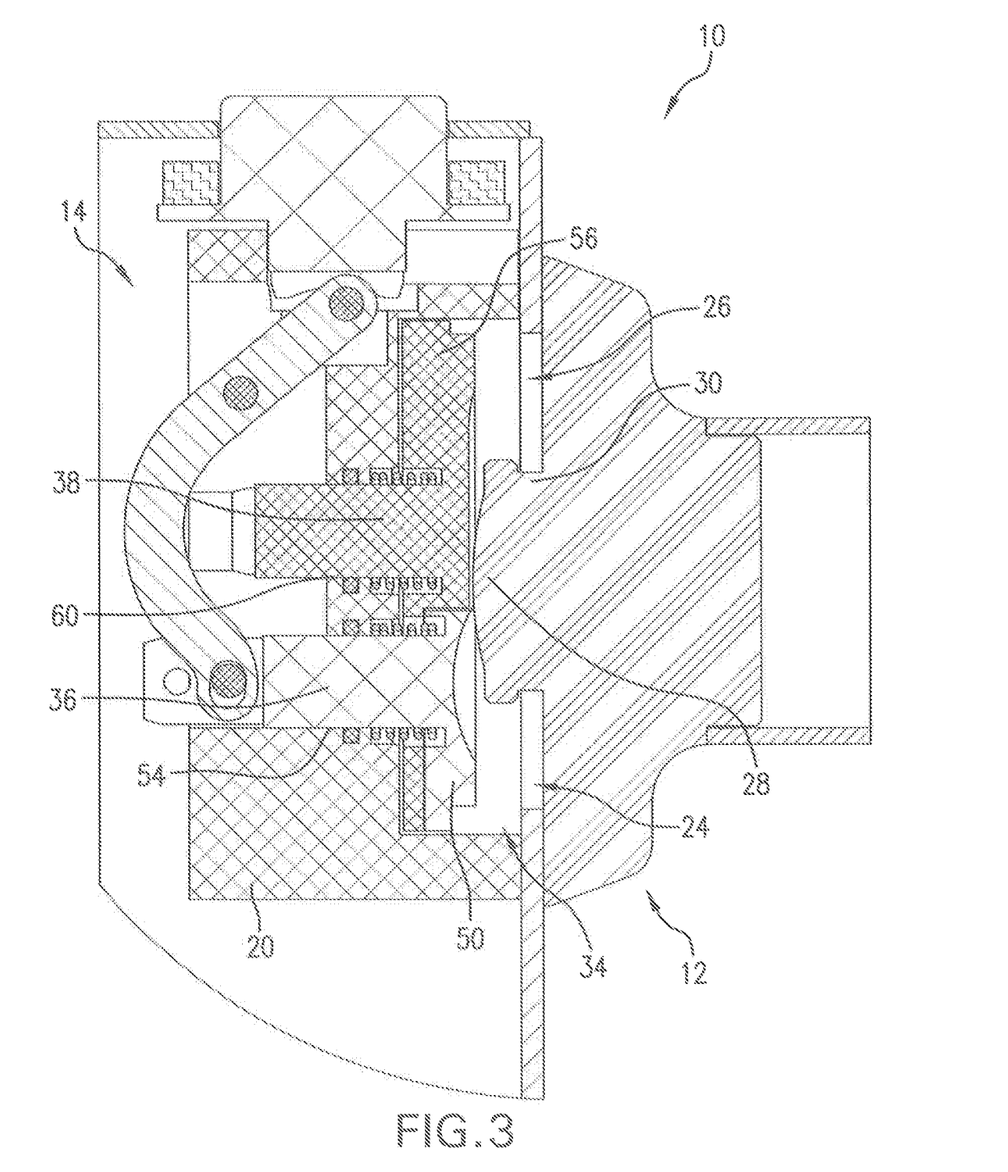
FIG. 3 is a cross-sectional view of the mount interface shown in FIG. 1, wherein the latch is between the second position and the third position.

FIGS. 2, 3 and 4 illustrate the latch 12 moving from the second position to a position of maximum lateral movement within the cavity 34, which may be referred to as the third position. As the head portion 28 of the latch 12 moves from the second position to the third position, the head portion 28 slides along the heads 50, 56 so that the pressing force exerted by the head portion 28 of the latch 12 is transferred from the head 50 of the first plug 36 to the head 56 of the second plug 38. Thus, once the latch 12 has reached the third position, as shown in FIG. 4, the head portion 28 of the latch 12 engages the head 56 of the second plug 38 and does not engage the head 50 of the first plug 36. Consequently, in the third position, the latch 12 presses against the head 56 of the second plug 38 so as to maintain the second plug 38 in the tensioned-spring position; however, the first plug 36 is free to move back to the spring-biased rest position, which it does.

Thus, when the head portion 28 of the latch 12 is in the third position, the first plug 36 is moved by its spring 40 back to the spring-biased rest position, thereby plugging the first portion 24 of the irregular orifice 22 and locking the latch 12 in the elongated portion 26 of the irregular orifice 22. In this way, the head portion 28 of the latch 12 is locked in the cavity 34 so that the latch 12 is securely latched to the latching assembly 14. Furthermore, the head 50 of the first plug 36 and the base portion 32 of the latch 12 abut one another so as to occlude the irregular orifice 22 and prevent blood, other bodily fluids, and/or other substances, from entering cavity 34. In order to unlatch the latch 12 from the latching assembly 14, the latching assembly 14 is provided with a lock release assembly 80.

The lock release assembly 80 includes a link member 82 that is pivotally connected to the housing 20, and that is connected at one end to the tail portion 52 of the first plug 36 and at another end to a release button 84. A pivot pin 86 is used to pivotally connect the link member 82 to the housing 20, and pins 88 and 90 are used to connect the link member 82 to the tail portion 52 of the first plug 36 and to the release button 84, respectively. The link member 82 may be non-linear, and it may include a linear portion 92 connected to a minor bend portion 94 by a major bend portion 96, wherein the radius of curvature of the major bend portion 96 is directed to a side of the link member 82 that is opposite the side of the link member 82 towards which the radius of curvature of the minor bend portion 94 is directed. The minor bend portion 94 may be provided with a slot 98 formed therein, and in which the pin 88 extends, in order to provide more play in movement for the pin 88 than a round hole.

Figure 5:
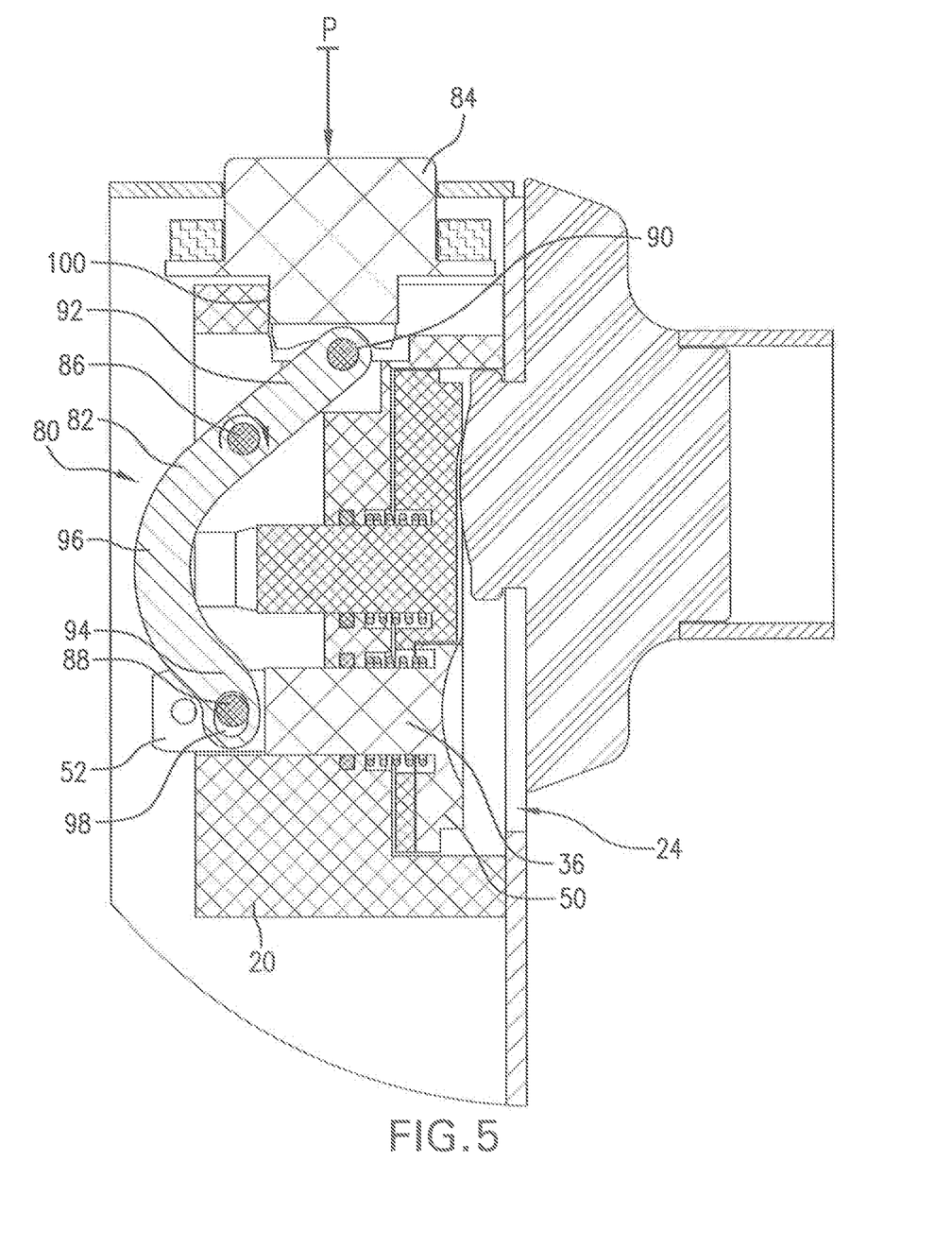
FIG. 5 is a cross-sectional view of the mount interface shown in FIG. 1, wherein the latch is in the third position and the lock release assembly has been activated so the first plug is in the tensioned-spring position.

As evident from FIGS. 4 and 5, when an external pressure P is applied to the release button 84 so as to depress the release button 84 in a channel 100 formed in the housing 20, the link member 82 is forced to rotate clockwise about pivot pin 86, which causes the end of the link member 82 connected to the tail portion 52 of the first plug 36 to pull the first plug from the spring-biased rest position to the tensioned-spring position. As a result, the head 50 of the first plug 36 is moved out of the first portion 24 of the irregular orifice 22 so the latch 12 is free to slide from the elongated portion 26 to the first portion 24 of the irregular orifice 22 by sliding over the head 56 of the second plug 38 and then over the head 50 of the first plug 36.

Figure 7:
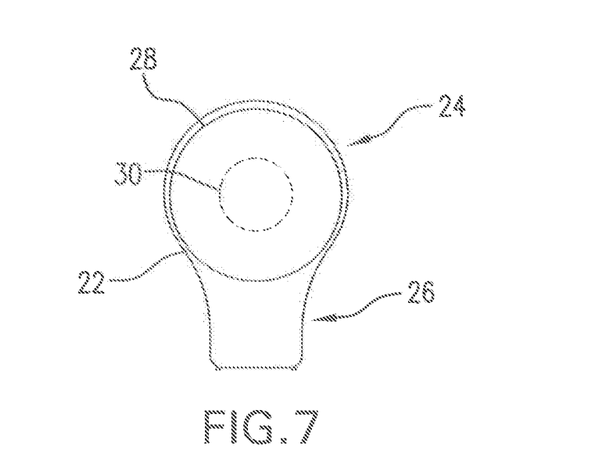
FIG. 7 is a schematic drawing illustrating an embodiment of an irregular orifice and its size relationship with respect to a latch in accordance with an embodiment of this disclosure.

Thus, after the first plug 36 has been moved from the spring-biased rest position to the tensioned-spring position by pressure activation of the lock release assembly 80, then the latch 12 is no longer locked in the third position, as evident from FIG. 5, but is free to move from the third position back to the second position. Once the latch 12 is in the second position, then it is possible to remove the latch 12 from the cavity 34 and from the irregular orifice 22 because the first portion 24 of the irregular orifice 22 is larger in size than the head portion 28 of the latch 12, such as shown in FIG. 7.

Figure 8:
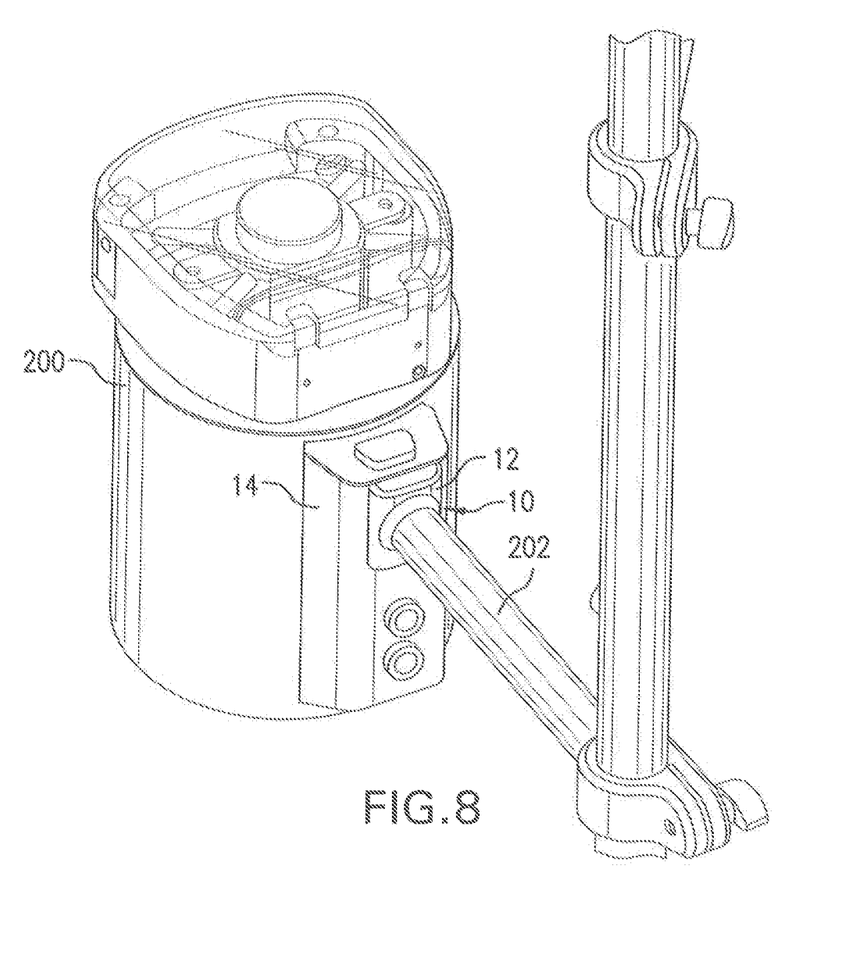
FIG. 8 is a perspective view of a mount interface in accordance with an embodiment of this disclosure, deployed in a non-limiting environment.
Figure 9:
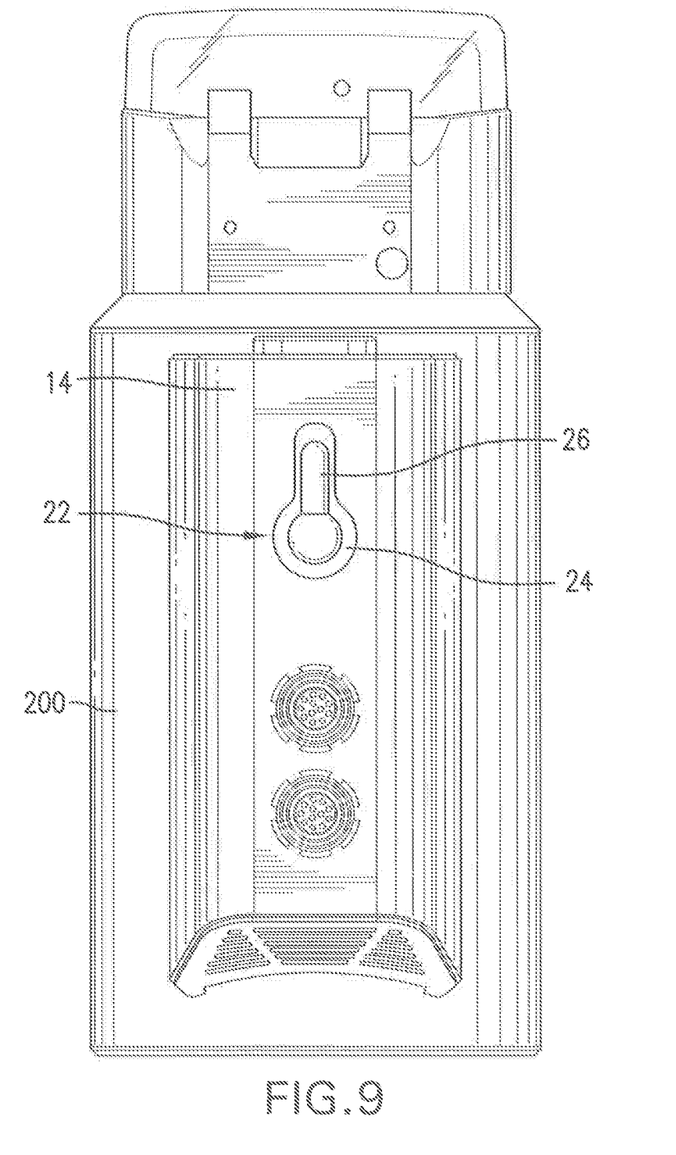
FIG. 9 is a front three-dimensional view of a latching assembly connected to a medical device.

FIGS. 8 and 9 illustrate a mount interface 10, in accordance with an embodiment of this disclosure, employed so at to mount a medical device 200, such as a heavy cardiac pump, to the frame 202 of a cardiopulmonary bypass machine. The medical device 200 is not limited to a cardiac pump, such as a centrifugal pump, for it may be a venous reservoir, an oxygenator, a venous clamp, or an accessory table. Thus, the mount interface 10 makes it possible to mount such substantially different medical devices on different places on the frame 202 of the cardiopulmonary bypass machine provided with multiple latches 12, thereby permitting interchangeability and flexibility with respect to configuring such medical devices on the frame 202 of the cardiopulmonary bypass machine. In accordance with an embodiment of this disclosure, the device 200 does not have to be a medical device, and the frame 202 does not have to be a frame of a cardiopulmonary bypass machine, or other heart-lung machine. In accordance with an embodiment of this disclosure, the mount interface 10 is deployable in any environment in which there is a need to mount one device to the frame of another device.

While systems and methods have been described with reference to certain embodiments within this disclosure, one of ordinary skill in the art will recognize, that additions, deletions, substitutions and improvements can be made while remaining within the scope and spirit of the invention as defined by the appended claims.

What is claimed is:

1. A method of locking a latch to a latching assembly of a mount interface, wherein the method comprises the steps of:
engaging a latch with a spring-biased first plug of the latching assembly, the spring-biased first plug being disposed in a housing of the latching assembly;
pressing the latch against the spring-biased first plug so as to insert the latch into a first portion of an irregular orifice of the housing of the latching assembly while moving the spring-biased first plug from a spring-biased rest position to a second position and while moving a spring-biased second plug from a spring-biased rest position to a second position so that the spring-biased first plug and the spring-biased second plug move parallel to one another, the spring-biased second plug being disposed in the housing of the latching assembly; and
sliding the latch from the first portion of the irregular orifice to a second portion of the irregular orifice so the latch presses against the spring-biased second plug and not against the spring-biased first plug.

2. The method according to claim 1, wherein the first portion of the irregular orifice is circular and the second portion of the irregular orifice is non-circular, and when the latch is in the second portion of the irregular orifice, the spring-biased second plug pushes the latch against the housing.

3. The method according to claim 1, further comprising the step of:
   locking the latch in the second portion of the irregular orifice when the spring-biased first plug moves back to the spring-biased rest position from the second position.

4. The method according to claim 3, further comprising the steps of:
   pressing a release button so as to cause the spring-biased first plug to move away from the spring-biased rest position and back to the second position in order to release the latch from the second portion of the irregular orifice;
   sliding the latch from the second portion of the irregular orifice to the first portion of the irregular orifice; and
   disengaging the latch from the spring-biased first plug of the latching assembly.

* * * * *